US00PP15485P2

(12) United States Plant Patent
Trees

(10) Patent No.: US PP15,485 P2
(45) Date of Patent: Jan. 25, 2005

(54) ***NEMESIA* PLANT NAMED 'BALARROPI'**

(50) Latin Name: *Nemesia×hybrida*
Varietal Denomination: Balarropi

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 148 days.

(21) Appl. No.: 10/107,515

(22) Filed: Mar. 26, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Wood, Phillips, Katz, Clark & Mortimer

(57) ABSTRACT

A new and distinct *Namesia* plant named 'Balarropi', characterized by its pink flowers, compact, semi-upright growth habit, and medium green leaves.

2 Drawing Sheets

Latin name of the genus and species of plant claimed: *Nemesia×hybrida.*

Variety denomination: 'Balarropi'.

BACKGROUND OF THE INVENTION

The present invention comprises a new and distinct *Nemesia* plant, botanically known as *Nemesia×hybrida,* and hereinafter referred to by the cultivar name 'Balarropi'.

The new cultivar is the result of open pollination with the female parent being 'Compact Innocence' (cultivar name 'Tiktok' U.S. Plant Pat. No. 10,977), which exhibits white flowers and a trailing habit and the male parent being a mix of pollen from unknown field selections (not patented). The new cultivar was discovered as a single flowering plant within the progeny of the above stated cross during 2000, in a controlled environment at Arroyo Grande, Calif. The new cultivar was initially designated 'NEM-108'.

Asexual reproduction of the new cultivar has been carried out at Arroyo Grande, Calif. and West Chicago, Ill. by terminal tip cuttings and has demonstrated that the characteristics of the new cultivar as herein described are firmly fixed and retained through successive generations of such asexual propagation.

SUMMARY OF THE INVENTION

It was found that the cultivar of the present invention:

(a) exhibits pink flowers;

(b) forms medium green foliage;

(c) exhibits a good basal branching character; and (d) exhibits a compact, semi-upright growth habit.

The new cultivar of the present invention can be compared to its female parent, 'Compact Innocence' (U.S. Plant Pat. No. 10,977). In side-by-side comparisons, plants of the new cultivar exhibit a shorter growth habit, have shorter pedicels, larger leaves and different flower color than 'Compact Innocence'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 10 weeks in a greenhouse at West Chicago, Ill.

Photograph A illustrates the overall growth habit of the new cultivar with three plants per pot.

Photograph B illustrates individual flowers of the new cultivar.

DETAILED BOTANICAL DESCRIPTION

The cultivar 'Balarropi' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Oct. 15, 2001. The readings were taken between 1:00 and 3:00 p.m. under natural daylight conditions. The plants were produced from cuttings taken from stock plant and were grown in a double polycarbonate covered greenhouse under conditions comparable to those used in commercial practice. The plants were grown utilizing a soilless growth medium and maintaining temperatures of approximately 48° to 60° F. (9° to 16° C.) during the night and light levels of 4,000 to 7,000 footcandles. Plants used for the following descriptions and measurements were grown in 10 cm pots for 10 weeks from rooted cuttings.

Classification:

*Botanical.*—*Nemesia×hybrida* cultivar 'Balarropi'.

Parentage:

*Female parent.*—'Compact Innocence'.

*Male parent.*—Mix of pollen from unknown field selections.

Propagation:

*Type cutting.*—Terminal tip.

*Time to initiate roots.*—Approximately 7 to 10 days.

*Time to develop roots.*—Approximately 14 to 21 days.

*Root description.*—Fibrous, branching.

Plant description:

*Habit of growth.*—Compact and freely branching. Pinching improves basal branching. A mature plant, 8 to 10 weeks after the planting of a rooted cutting, commonly measures approximately 16.8 cm in height and approximately 36.1 cm in diameter with an average of 5 branches.

*Form.*—Spreading and trailing.

*Stem.*—Approximately 25.5 cm in length and approximately 2 mm in diameter, glabrous and 146A. Internode length at middle of branch is approximately 4 cm.

*Foliage.*—Leaves are non-fragrant, single, opposite, at an acute angle to the stem with an average of 9.6 leaves per lateral branch. Leaves are narrow ovate with serrate margin, acute apex and attenuate base. Upper and lower surfaces are glabrous. Leaf length is approximately 3.9 cm and width is approximately 1.6 cm. Upper surface of mature foliage is 147A, lower surface of mature foliage is 147B. Both upper and lower surfaces have palmate venation closest to 147A. Petiole length is approximately 3.2 mm, diameter is approximately 3.3 mm, surface is glabrous and color is closest to 144B.

Flowering description:

*Flowering habit.*—Freely flowering.

*Natural flowering season.*—Year round in greenhouse environment and spring through autumn in outdoor garden.

*Inflorescence type.*—Terminal clusters.

*Terminal cluster.*—Diameter is approximately 3.1 cm and height is approximately 2.5 cm. There are an average of 7.4 flowers per cluster and an average of 19 open clusters per plant.

*Peduncle.*—Strong, glabrous, at an acute angle to the stem, approximately 5.6 cm in length and 1 mm in diameter. Peduncle color is 146A.

*Bud.*—Round, approximately 6 mm in length, 6 mm in diameter. Bud tip color is 65C.

*Flower description.*—Length is approximately 1.4 cm and width is approximately 1.3 cm. Flowers are bilabiate, the upper lip has three obvate lobes with rounded tips, attenuate bases and the lower lip has two obvate lobes with rounded tips, attenuate bases. When first open, the upper surface of the lobes is 72C with spot of 2A on lower lip at the palate. Upper surface of mature lobes is 77C with veins of 77B. Color of the lower surface of all lobes, either when first opening or at maturity is 65C.

*Nectary.*—Quantity per flower: One. Length is 6 mm and color is 3D.

*Calyx.*—Five sepals fused as base, approximately 3 mm in length. Lower two sepals are oblanceolate, upper three sepals are linear, less than 1 mm in width, have an acute apex and entire margin. Both surfaces are slightly pubescent and 137A.

*Lastingness of bloom.*—Approximately 5 days.

*Reproductive organs.*—Androecium: These are 4 stamens — 2 are 8 mm in length, 2 and 6 mm in length. Anthers are 1 mm in length. Pollen is abundant and color is 13B. Gynoecium: One pistil, 3 mm in length. Stigma is less than 1 mm in length and 150C. Style length is less than 1 mm and color is 150D. Ovary diameter is 2 mm and color is 144A.

Seed production: Seed production has not been observed.

Disease resistance: Resistance to pathogens has not been observed.

Hardiness zone: 'Balarropi' is hardy in zones nine (9) and above.

I claim:

1. A new and distinct cultivar of *Nemesia* plant named 'Balarropi' substantially as herein shown and described, which:

(a) exhibits pink flowers;

(b) medium green foliage;

(c) a good basal branching character; and (d) a compact, semi-upright growth habit.

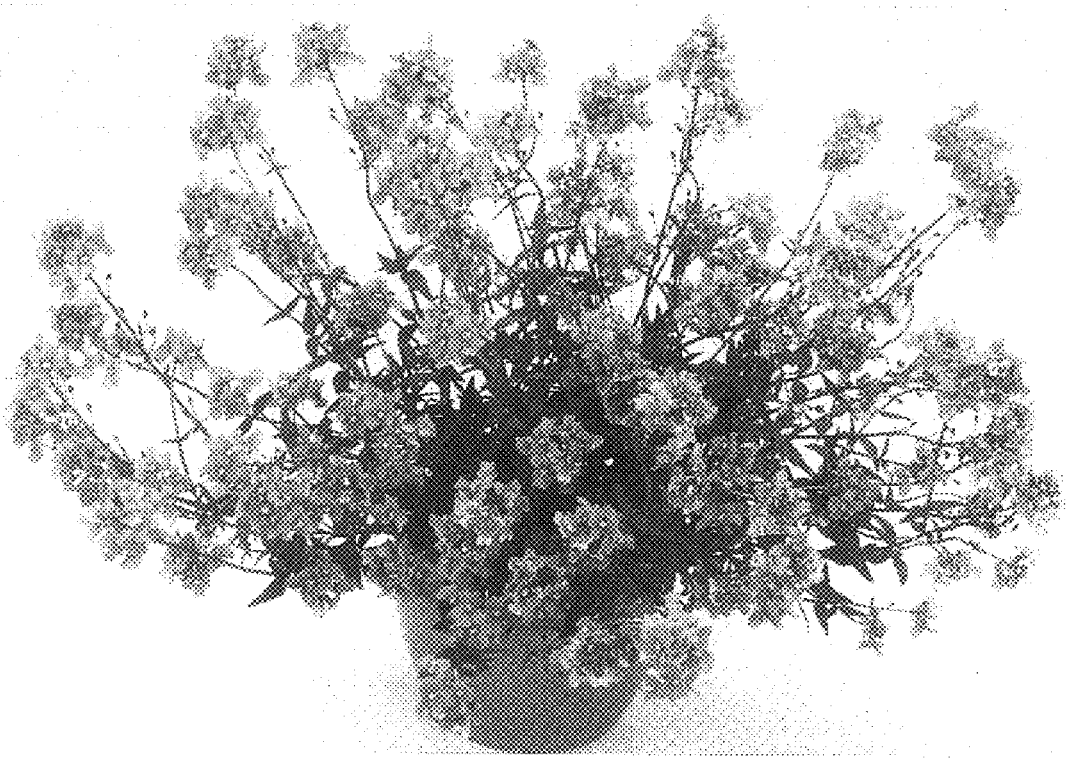

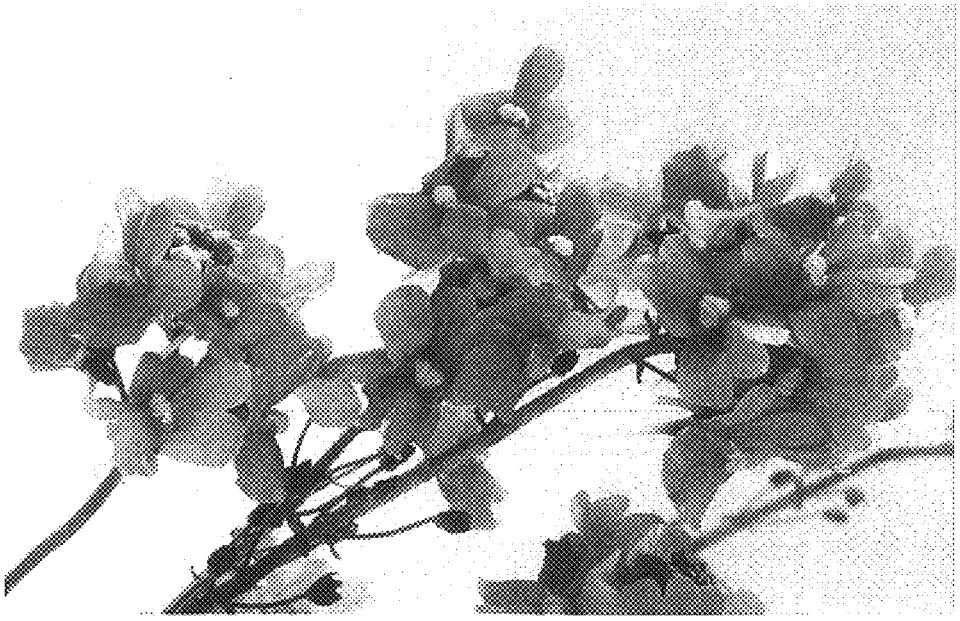

* * * * *